United States Patent [19]

Kainmüller et al.

[11] Patent Number: 5,171,873
[45] Date of Patent: Dec. 15, 1992

[54] PROCESS FOR THE PREPARATION OF STERICALLY HINDERED HYDROXYBENZYLPHOSPHONATES

[75] Inventors: Thomas Kainmüller, Lindenfels; Rudolf Maul, Lorsch/Hessen, both of Fed. Rep. of Germany

[73] Assignee: Ciba-Geigy Corporation, Ardsley, N.Y.

[21] Appl. No.: 861,704

[22] Filed: Apr. 1, 1992

[30] Foreign Application Priority Data

Apr. 5, 1991 [CH] Switzerland ............... 1016/91

[51] Int. Cl.$^5$ ............................. C07F 9/40
[52] U.S. Cl. ............................. 558/122; 558/194
[58] Field of Search ................. 558/122, 194

[56] References Cited

U.S. PATENT DOCUMENTS

| | | | |
|---|---|---|---|
| 3,006,945 | 10/1961 | Goddard et al. | 558/125 |
| 3,155,704 | 11/1964 | Knapp | 558/125 |
| 3,268,630 | 8/1966 | Spivack | 558/122 |
| 3,280,070 | 10/1966 | Di Battista et al. | 524/131 |
| 3,281,505 | 10/1966 | Spivack | 558/194 |
| 3,367,870 | 2/1968 | Spivack | 252/49.8 |
| 3,787,540 | 1/1974 | Schmidt et al. | 558/134 |
| 3,790,648 | 2/1974 | Schmide et al. | 558/134 |
| 4,263,232 | 4/1981 | Parekh | 558/146 |

FOREIGN PATENT DOCUMENTS 1487609 10/1977 United Kingdom .

OTHER PUBLICATIONS

Derwent Abst. 73-63841u/43; DE 2,312,910 (1974).
Ovchinnikor et al., Cyclic Phosphoorganic Compounds With an Active Methylene Group p. 834 (1981).

Primary Examiner—Mary C. Lee
Assistant Examiner—Michael G. Ambrose
Attorney, Agent, or Firm—Luther A. R. Hall

[57] ABSTRACT

A process for the preparation of hydroxybenzylphosphonates of forula

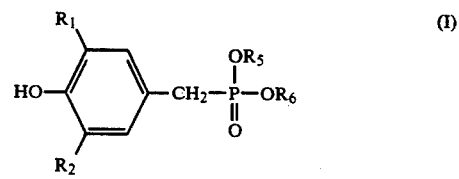

(I)

by reacting Mannich base of formula

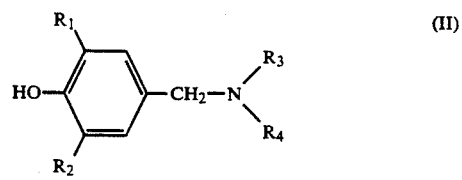

(II)

with as trialkyl phosphite of formula

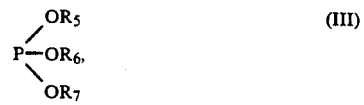

(III)

wherein $R_1$ and $R_2$ are each independently of the other $C_1$–$C_{12}$alkyl or, when taken together form a piperidinyl or morpholinyl radical, and $R_5$, $R_6$ and $R_7$ are each independently of one another $C_1$–$C_4$alkyl, which reaction is carried out in the presence of a carboxylic anhydride (IV).

The compounds of formula I may suitably be used as processing stabilizers for plastics.

10 Claims, No Drawings

PROCESS FOR THE PREPARATION OF STERICALLY HINDERED HYDROXYBENZYLPHOSPHONATES

The present invention relates to a process for the preparation of sterically hindered hydroxybenzylphosphonates by reacting 3,5-di(cyclo)alkyl-4-hydroxybenzylamines with trialkylphosphites and carboxylic anhydrides.

Sterically hindered hydroxybenzylphosphonates are used, inter alia, as processing stabilisers for plastics. A number of processes for their preparation are known from the literature, in which connection reference is made to the following publications: U.S. Pat. No. 3,790,648, U.S. Pat. No. 3,006,945, SU-A 619 486, DE-A 2 222 708, FR-A 1 382 891).

A group of these reactions utilises the reaction with the readily obtainable Mannich bases of formula

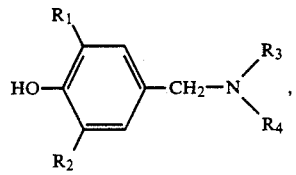

wherein the substituents $R_1$ to $R_4$ may have the meanings given below.

The quaternisation of such Mannich bases with methyl iodide and reaction of the ammonium salts with trialkylphosphites is disclosed in U.S. Pat. No. 3,155,704 and DE-A 2 312 910. Methyl iodide, however, is not only rather expensive but also a dangerous carcinogen and must therefore be handled only under stringent safety conditions. In addition, the quaternary ammonium salts are as a rule poorly soluble in inexpensive non-polar aprotic solvents and can result in incrustations.

In the process described in U.S. Pat. No. 3,790,648, the Mannich bases are reacted in the presence of alkali metals or the hydrides or amides thereof with dialkyl phosphites. This process requires the use of strongly basic solids and, if inexpensive dimethylamine is used to prepare the Mannich base, the former would have to be recovered in the form of a product which is gaseous at room temperature using complicated apparatus, as it is generated during the reaction. The particular susceptibility of starting materials and products to the presence of strong alkalies leads to the formation of discoloured products. Although this drawback can be avoided by the process disclosed in U.S. Pat. No. 4,263,232, the yields are unsatisfactory. Moreover, there is the danger of undesirable saponification of the products.

The direct reaction of Mannich bases with trialkyl or dialkyl phosphites is disclosed in DE-A 2 456 532 and by V. V. Ovchinnikow et al. in Zh. Obshch. Khim. 51, 999 (1981). The drawbacks of this process are the lengthy reaction times and the fact that free amine is formed as by-product.

Alternatives to the Mannich bases, in which bromide or acetate replaces the amino group, are also disclosed in DE-A 2 312 910. The compounds are isolated before the reaction with phosphites, and the total yields are substantially lower than when using the corresponding Mannich bases.

Hence there is still a need to provide a novel process which solves one or more of these problems.

Surprisingly, it has now been found that hydroxybenzylphosphonates of formula

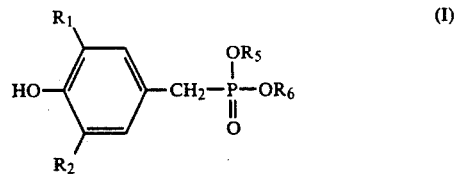

can be prepared in good yield and substantially avoiding discolourations, using inexpensive and toxicologically more acceptable reagents, by reacting a Mannich base of formula

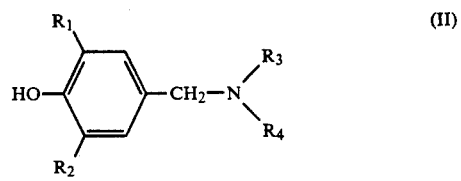

with a trialkyl phosphite of formula

wherein $R_1$ and $R_2$ are each independently of the other $C_1$–$C_{12}$alkyl or $C_5$–$C_7$cycloalkyl, $R_3$ and $R_4$ are each independently of the other $C_1$–$C_{12}$alkyl or, when taken together, form a piperidinyl or morpholinyl radical, and $R_5$, $R_6$ and $R_7$ are each independently of one another $C_1$–$C_4$alkyl, which reaction is carried out in the presence of a carboxylic anhydride (IV).

$R_1$, $R_2$, $R_3$ and $R_4$ defined as $C_1$–$C_{12}$alkyl in the above formulae are branched or unbranched radicals. Such radicals are typically methyl, ethyl, propyl, isopropyl, n-butyl, isobutyl, tert-butyl, pentyl, isopentyl, hexyl, heptyl, 3-heptyl, octyl, 2-ethylhexyl, nonyl, decyl, undecyl, ddecyl, 2-ethylbutyl, 1-methylpentyl, 1,3-dimethylbutyl, 1,1,3,3-tetramethylbutyl, 1-methylhexyl, isoheptyl, 1-methylheptyl, 1,1,3-trimethylhexyl or 1-methylundecyl. $R_5$, $R_6$ and $R_7$ as $C_1$–$C_4$alkyl may suitably be methyl, ethyl, propyl, isopropyl, n-butyl, isobutyl and tert-butyl.

$R_1$ and $R_2$ as $C_5$–$C_7$cycloalkyl may be cyclopentyl, cyclohexyl or cycloheptyl.

A useful embodiment of the invention comprises carrying out the reaction such that the amount of phosphite does not fall below that of the anhydride in the course of the reaction.

The carboxylic anhydride (IV) may be derived from any carboxylic acids. Exemplary of such anhydrides are acetic anhydride, succinic anhydride, phthalic anhydride, tetrahydrophthalic anhydride, methyltetrahydrophthalic anhydride (predominantly as mixture of isomers) as well as hexahydrophthalic anhydride. It is preferred to use acetic anhydride, phthalic anhydride or hexahydrophthalic anhydride, preferably acetic anhydride.

The reaction temperatures are conveniently in the range from room temperature to 200° C., preferably from 50° to 140° C. and, most preferably, from 60° to 120° C.

The reaction is expediently carried out under atmospheric (normal) pressure.

The reaction can be carried out without a solvent; but the presence of an organic, preferably aprotic, solvent is useful. This solvent may be non-polar or polar. Exemplary of polar aprotic solvents are dimethyl formamide, dimethyl acetamide and N-methylpyrrolidone. Preferred solvents are aprotic and non-polar, conveniently aliphatic hydrocarbons, typically heptane, octane, cyclohexane, decalin, mineral oil distillates such as petroleum ether, ligroin, kerosene, aromatic hydrocarbons such as benzene, toluene or xylenes, or mixtures of said solvents.

Especially preferred solvents are petroleum ether fractions, benzene, toluene and the xylene isomers, most preferably the petroleum ether fraction 100/140 (gasoline), benzene and toluene.

The process is particularly suitable for preparing compounds of formula I, wherein $R_1$ and $R_2$ are each independently of the other $C_1$-$C_6$alkyl or cyclohexyl, and $R_3$ and $R_4$ are each independently of the other $C_1$-$C_6$alkyl or, when taken together, form a piperidinyl or morpholinyl radical.

The process is especially suitable for the preparation of compounds of formula I, wherein $R_1$ and $R_2$ are tert-butyl radicals. In this case the yields are especially high.

The starting materials II, III and IV are conveniently used in approximately equimolar amounts (but an excess of up to 20%, preferably of up to 10%, of one or more of the reactants can be useful, for example of the phosphite and/or of the anhydride), preferably such that II and III are charged to the reactor and IV is added over a period of time which, depending on the size of the batch, can be up to several hours. By means of this procedure, the amount of phosphite does not fall below that of the anhydride during the reaction.

Working up of the products of formula I is effected by conventional methods, typically by washing out the water-soluble by-products, recrystallisation and the like. Normally water is added to the reaction mixture to remove water-soluble reaction products. The desired product precipitates upon the addition of water or after removal of water from the reaction mixture. The precipitate can then be filtered with suction and washed with the solvent used. The reaction products of the carboxylic anhydride, for example compounds of the type R—CO—O—$R_{5,6,7}$ or R—CO—NR$_3$R$_4$, R—CO is the acid radical of the anhydride, normally remain in solution or, upon washing, pass into the aqueous phase.

The starting Mannich bases of formula II can be obtained almost quantitatively from a dialkyl phenol

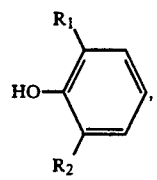

formaldehyde and a secondary amine

as disclosed, inter alia, in DE-A 2 312 910.

The compounds prepared by the novel process may suitably be used as stabilisers for protecting numerous organic monomers and polymers against degradation induced by heat, oxidation and/or photo-oxidation, as disclosed, inter alia, in U.S. Pat. No. 3,280,070, U.S. Pat. No. 3,281,505 and U.S. Pat. No. 3,367,870.

The invention is illustrated in more detail by the following non-limitative Examples in which, and throughout the remainder of the description, parts and percentages are by weight, unless otherwise indicated.

EXAMPLE 1

A thermostatically controllable reactor is charged with 553.8 g (2.1 mol) of (4-hydroxy-3,5-di-tert-butylbenzyl)dimethylamine und 450 g of petroleum ether 100/140. With stirring and blanketing with inert gas, the reaction mixture is heated to 60° C. and 366.4 g (2.2 mol) of triethyl phosphite are run into the clear solution. With cooling, 225.1 g (2.2 mol) of acetic anhydride are then added dropwise over 2 hours at 60° C., and stirring is continued for 1 hour at 60° C. The solvent is removed by distillation until the temperature is 115° C. The residual reaction solution is washed with 4×250 ml of water at 75° C. and dried by azeotropic distillation. Upon cooling to room temperature, the product crystallises and is filtered with suction, washed with petroleum ether 100/140 and dried, giving 693.2 g (92.6% of theory) of colourless diethyl 4-hydroxy-3,5-di-tert-butylbenzylphosphonate of m.p. 119°–121° C.

EXAMPLE 2

A thermostatically controllable reactor is charged with 263 g (1 mol) of (4-hydroxy-3,5-di-tert-butylbenzyl)dimethylamine und 500 g of petroleum ether 100/140. With stirring and blanketing with inert gas, the reaction mixture is heated to 80° C. and 130 g (1.05 mol) of trimethyl phosphite are run into the clear solution. With cooling, 107 g (1.05 mol) of acetic anhydride are then added dropwise over 2 hours at 80° C., and stirring is continued for 2 hours at 80° C. The solvent is removed by distillation until the temperature is 115° C. The residual reaction solution is cooled to room temperature and stirred with 1 liter of water. The crystallised product is filtered with suction, washed with petroleum ether 100/140 and dried, giving 307 g (93% of theory) of almost colourless dimethyl 4-hydroxy-3,5-di-tert-butylbenzylphosphonate of m.p. 156°–160° C.

EXAMPLE 3

A thermostatically controllable reactor is charged with 13.1 g (0.073 mol) of (4-hydroxy-3,5-dimethyllbenzyl)dimethylamine und 20 g of petroleum ether 100/140. With stirring and blanketing with inert gas, the reaction mixture is heated to 80° C. and 12.2 g (0.073 mol) of triethyl phosphite are run into the clear solution. Then 7.5 g (0.073 mol) of acetic anhydride are added dropwise over 1 hour with cooling, and stirring is continued for 1 hour at 80° C. Working up is carried out in accordance with the general procedure of Example 2, giving 16.9 g (85% of theory) of diethyl 4-hydroxy-3,5-dimethylbenzylphosphonate of m.p. 70°–71° C.

What is claimed is:

1. A process for the preparation of a hydroxybenzylphosphonate of formula

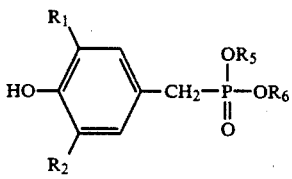
(I)

by reacting a Mannich base of formula

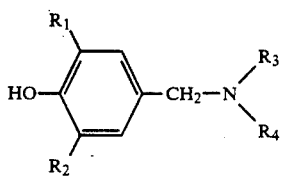
(II)

with a trialkyl phosphite of formula

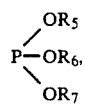
(III)

wherein $R_1$ and $R_2$ are each independently of the other $C_1$–$C_{12}$alkyl or $C_5$–$C_7$cycloalkyl, $R_3$ and $R_4$ are each independently of the other $C_1$–$C_{12}$alkyl or, when taken together, form a piperidinyl or morpholinyl radical, and $R_5$, $R_6$ and $R_7$ are each independently of one another $C_1$–$C_4$alkyl, which reaction is carried out in the presence of a carboxylic anhydride (IV).

2. A process according to claim 1, wherein the amount of phosphite does not fall below that of the anhydride in the course of the reaction.

3. A process according to claim 1, wherein $R_1$ and $R_2$ in formula II are each independently of the other $C_1$–$C_6$alkyl or cyclohexyl and $R_3$ and $R_4$ are each independently of the other $C_1$–$C_6$alkyl or, when taken together, form a piperidinyl or morpholinyl radical.

4. A process according to claim 1, wherein $R_1$ and $R_2$ in formulae I and II are tert-butyl radicals.

5. A process according to claim 1, wherein the carboxylic anhydride is acetic anhydride, phthalic anhydride or hexahydrophthalic anhydride.

6. A process according to claim 1, wherein the reaction temperature is in the range from room temperature to 200° C.

7. A process according to claim 6, wherein the the reaction temperature is in the range from 50° to 140° C.

8. A process according to claim 6, wherein the the reaction temperature is in the range from 60° to 120° C.

9. A process according to claim 1, which is carried out in an aprotic and non-polar solvent.

10. A process according to claim 9, which is carried out in a solvent selected from the group consisting of petroleum ether 100/140 (gasoline), benzene or toluene.

* * * * *